(12) United States Patent
Anderson

(10) Patent No.: US 7,302,948 B2
(45) Date of Patent: Dec. 4, 2007

(54) FLUID DISPENSING DEVICE

(75) Inventor: Gregor John McLennan Anderson, Ware (GB)

(73) Assignee: Glaxo Group Limited, Brentford, Middlesex (GB)

( * ) Notice: Subject to any disclaimer, the term of this patent is extended or adjusted under 35 U.S.C. 154(b) by 436 days.

(21) Appl. No.: 10/504,711

(22) PCT Filed: Feb. 27, 2003

(86) PCT No.: PCT/GB03/00845

§ 371 (c)(1),
(2), (4) Date: Aug. 17, 2004

(87) PCT Pub. No.: WO03/074189

PCT Pub. Date: Sep. 12, 2003

(65) Prior Publication Data

US 2005/0098172 A1 May 12, 2005

(30) Foreign Application Priority Data

Mar. 1, 2002 (GB) .................................. 0204829.6

(51) Int. Cl.
*A61M 15/00* (2006.01)
(52) U.S. Cl. ..................... 128/200.14; 128/200.22; 128/205.18
(58) Field of Classification Search ............ 128/200.14, 128/200.22, 200.23, 203.12, 205.16, 205.18; 222/153.13, 182, 321, 384; 239/459, 333
See application file for complete search history.

(56) References Cited

U.S. PATENT DOCUMENTS 4,944,429 A * 7/1990 Bishop et al. ......... 222/153.13
4,946,069 A    8/1990 Fuchs
5,195,665 A    3/1993 Lina
5,226,563 A * 7/1993 Coggiola ..................... 222/95
5,408,994 A * 4/1995 Wass et al. ............ 128/203.15
5,429,122 A * 7/1995 Zanen et al. ........... 128/203.15
5,511,698 A * 4/1996 Solignac .................... 222/162
5,522,385 A * 6/1996 Lloyd et al. ........... 128/203.26
6,125,843 A   10/2000 Gold et al.
6,186,141 B1   2/2001 Pike et al.
6,189,739 B1   2/2001 Von Schuckmann
6,240,918 B1 * 6/2001 Ambrosio et al. ..... 128/203.15

(Continued)

FOREIGN PATENT DOCUMENTS

DE    19905993    8/2000

(Continued)

*Primary Examiner*—Steven O. Douglas
(74) *Attorney, Agent, or Firm*—Alice P. Bradney

(57) ABSTRACT

A fluid dispensing device comprising a body defining a cavity and a dispensing nozzle. A fluid discharging device is housed in the cavity. The fluid discharging device has a hollow casing defining a reservoir for containing a volume of fluid and a plunger slidingly engaged within the hollow casing. The plunger has a tubular portion which is arranged to extend from a first end of the hollow casing for co-operation with the dispensing nozzle. A biasing means is interposed between a second end of the hollow casing and an end wall of the cavity to bias the hollow casing towards the dispensing nozzle. A locking means holds the biasing means in a compressed state. Upon release of the locking means, the force stored in the biasing means is applied to the hollow casing thereby causing fluid to be ejected from the reservoir into the dispensing nozzle.

23 Claims, 4 Drawing Sheets

U.S. PATENT DOCUMENTS

| | | |
|---|---|---|
| 6,257,457 B1 | 7/2001 | Oechsel |
| 6,345,737 B1* | 2/2002 | Martin et al. ............... 222/320 |
| 6,397,839 B1* | 6/2002 | Stradella ................ 128/200.23 |
| 6,578,741 B2* | 6/2003 | Ritsche et al. ......... 222/153.13 |
| 6,708,846 B1* | 3/2004 | Fuchs et al. .................. 222/82 |
| 6,745,761 B2* | 6/2004 | Christrup et al. ...... 128/200.14 |
| 6,792,941 B2* | 9/2004 | Andersson ............. 128/200.23 |
| 2002/0011530 A1* | 1/2002 | Fuchs ........................ 239/333 |
| 2002/0074429 A1* | 6/2002 | Hettrich et al. ............. 239/333 |
| 2002/0134373 A1* | 9/2002 | Gonda .................. 128/200.14 |
| 2002/0183293 A1* | 12/2002 | Banerjee et al. ............ 514/171 |

FOREIGN PATENT DOCUMENTS

| | | |
|---|---|---|
| FR | 2682305 | 4/1993 |
| FR | 2714624 | 7/1995 |
| FR | 2758479 | 7/1998 |
| WO | WO 92/11049 | 7/1992 |
| WO | WO 99/28042 | 6/1999 |
| WO | WO 00/71262 | 11/2000 |
| WO | WO 01/43794 | 6/2001 |

\* cited by examiner

FLUID DISPENSING DEVICE

CROSS-REFERENCE TO RELATED APPLICATIONS

This application is filed pursuant to 35 USC 371 as a United States National Phase Application of International Patent Application Ser. No. PCT/GB03/00845 filed on Feb. 27, 2003 which claims priority from 0204829.6 filed on Mar. 1, 2002 in the United Kingdom.

FIELD OF THE INVENTION

The present invention relates to a medicament dispenser and in particular to fluid dispensing device for use as a nasal inhaler.

It is well known to provide a medicament dispenser in which fluid is dispensed via a nozzle or orifice upon the application of a force by a user to an actuation lever or button. Such devices may be arranged to dispense a single dose or may alternatively be arranged with a reservoir containing several doses to be dispensed. An example of such a pump action spray is shown and described in U.S. Pat. No. 4,946,069.

It is a problem with such prior art mechanical pumps that the efficacy of supply is dependent upon the manner in which the device is actuated by the user. If the user actuates the device in a slow or lethargic manner then the dispensing of the fluid is less efficient than if a rapid but constant pressure is brought to bear upon the actuation button or lever. In extreme cases the rate of discharge can be so low that full atomisation is unable to occur and the spray comprises of relatively large droplets of fluid.

It will be appreciated that the operation of such a device requires some manual dexterity and so if the patient has some problems with their hands the likelihood of an efficient dispensing is low.

It is an object of this invention to provide a fluid dispensing device that is easier to use and in particular a device which provides a repeatable dispensing of fluid.

SUMMARY OF THE INVENTION

According to a first aspect of the invention there is provided a fluid dispensing device comprising a body defining a cavity and a dispensing nozzle, a fluid discharging device housed in the cavity, the fluid discharging device having a hollow casing defining a reservoir for containing a volume of fluid and a plunger slidingly engaged within the hollow casing, the plunger having a tubular portion which is arranged to extend from a first end of the hollow casing for co-operation with the dispensing nozzle, biasing means interposed between a second end of the hollow casing and an end wall of the cavity to bias the hollow casing towards the dispensing nozzle and a locking means to hold said biasing means in a compressed state wherein upon release of the locking means the force stored in the biasing means is applied to the hollow casing thereby causing fluid to be ejected from the reservoir into the dispensing nozzle.

Suitably, the biasing means comprises a spring or other resiliently compressible mechanical member for storing mechanical energy.

In one aspect, the release of the biasing means from its compressed state acts such as to cause relative movement between the hollow casing and the plunger so as to eject a unit dose of fluid from the fluid reservoir into the dispensing nozzle.

The plunger may be slideable in a chamber located within the hollow casing, the chamber being sized to accommodate a single dose of fluid.

The re-setting of the biasing means into its compressed state may cause a new dose of fluid to be drawn into the chamber.

The reservoir may contain several doses of fluid.

The locking means may comprise of one or more detents, each of which is engageable with a respective aperture in a side wall of the body when the biasing means is in its compressed state.

Preferably, there may be several detents positioned for engagement with respective apertures in opposite side walls of the body.

The biasing means may be interposed between the end wall of the cavity and a support platform for the hollow casing.

Each detent may be connected to the support platform by a flexible limb.

Alternatively, each detent may be connected to the hollow casing by a flexible limb.

Preferably, each detent may include a portion, which extends outwardly from the side wall with which the detent is engaged to define a trigger that is operable by a user to release the biasing means from its compressed state.

The device may further comprise a protective end cap having an inner surface for engagement with the body to protect the dispensing nozzle.

The fitment of the protective end cap to the body may cause the resetting of the biasing means into its compressed state.

The hollow casing may have at least one outwardly extending lug for abutment with a complementary projection formed on the inner surface of the end cap to provide a driving connection therebetween.

The body may have at least one longitudinally extending slot through which a respective lug extends.

Preferably, there may be several lugs formed on the hollow casing for engagement with complementary projections formed on the inner surface of the end cap, each of the lugs being arranged to extend through a longitudinally extending slot formed in the side wall of the body.

The hollow casing may have at least one outwardly extending detent for engagement with a complementary recess formed in the inner surface of the end cap so as to releasable hold the end cap in position on the body.

Each detent may extend through a respective longitudinally extending slot in the body for engagement with the respective recess formed in the end cap.

According to a second aspect of the invention there is provided a fluid dispensing apparatus for housing a fluid discharging device, the fluid dispensing apparatus comprising a body defining a cavity, a dispensing nozzle, biasing means housed in the cavity and a locking means to selectively hold said biasing means in a compressed state, wherein, in use, a fluid discharging device is positioned between the biasing means and the dispensing nozzle.

The release of the locking means may cause the force stored in the biasing means to be applied to the fluid discharging device so as to bias the fluid discharging device towards the dispensing nozzle.

Suitably, the fluid discharging device comprises a pre-compression pump, such as a VP3, VP7 or modifications, model manufactured by Valois SA. Typically, such pre-compression pumps are used with a bottle (glass or plastic) capable of holding 8-50 ml of a formulation. Each spray will typically deliver 50-100 µl of such a formulation and the device is therefore capable of providing at least 100 metered doses.

The fluid dispensing apparatus may further comprise an end cap for engagement with the body wherein the end cap is adapted such that, in use, engagement of the end cap onto the body will cause compression of the biasing means.

BRIEF DESCRIPTION OF THE SEVERAL VIEWS OF THE FIGURES

The invention will now be described further with reference to the accompanying drawing in which.

DETAILED DESCRIPTION

Figure 1:
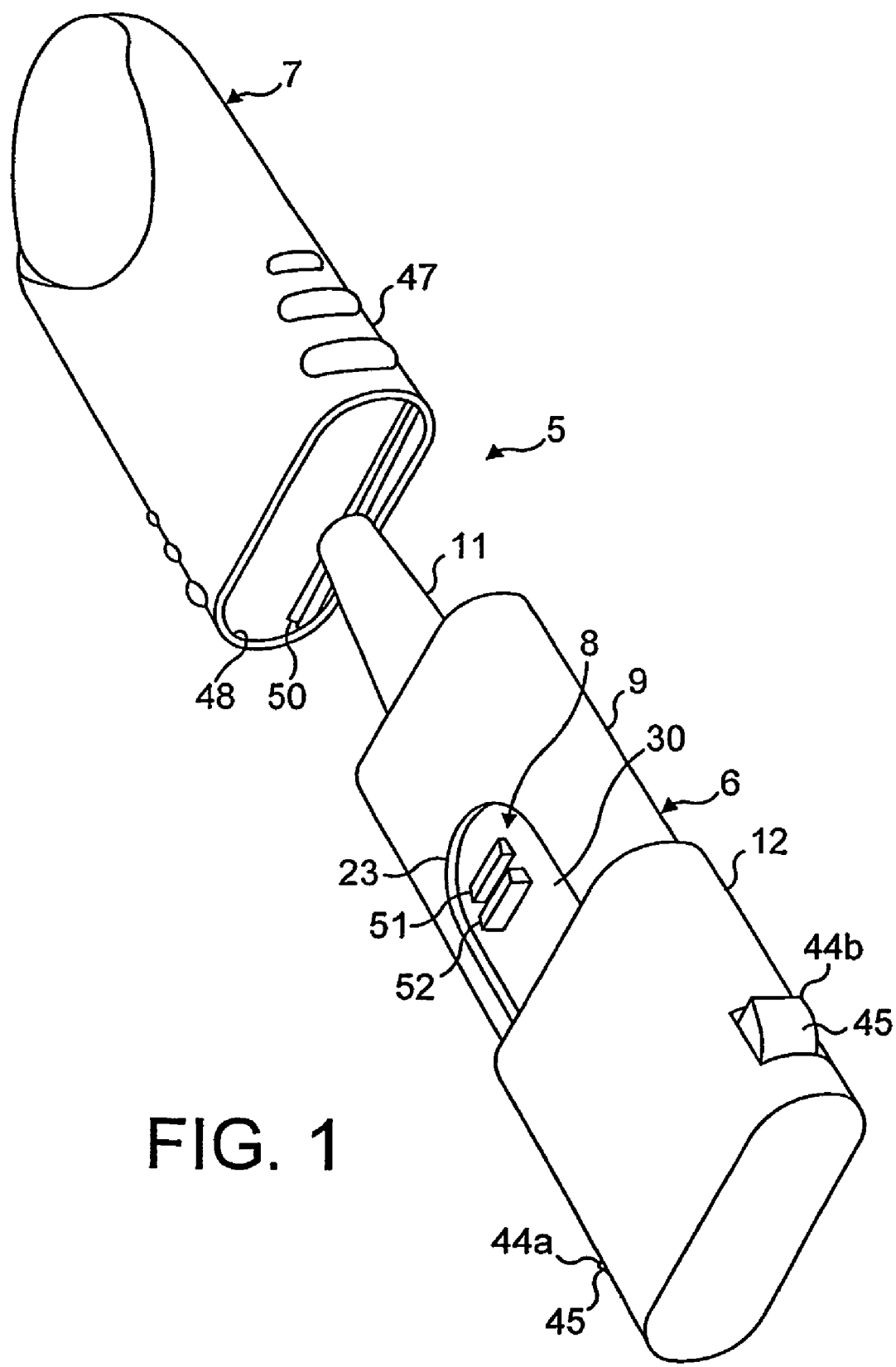
FIG. 1 shows an exploded view of a fluid dispensing device according to the invention.
Figure 2:
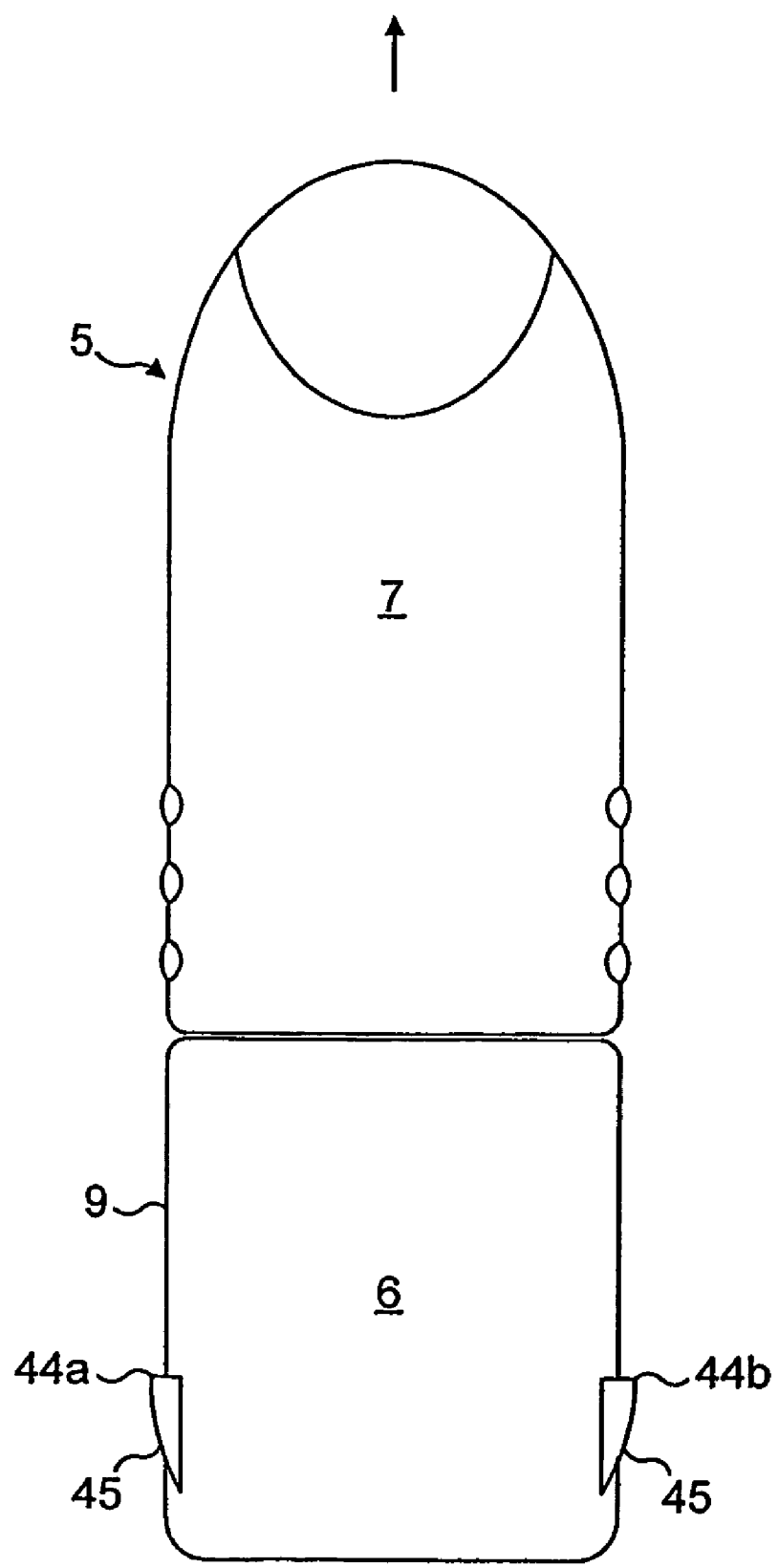
FIG. 2 shows a plan view of the fluid dispensing device shown in FIG. 1 in a closed or stored condition.

With reference to the figures there is shown a fluid dispensing device 5 comprising a body 6 and a fluid discharging device 8. The device further comprises a protective end cap 7 having an inner surface 48 for engagement with the body 6 to protect the dispensing nozzle 11.

The body 6 is made from a plastic material and defines a housing 9 and a dispensing nozzle 11.

The housing 9 defines a cavity 10 formed by a side wall 12 and first and second end walls 13 and 14. The dispensing nozzle 11 is connected to and extends away from the second end wall 14 and has an external tapering form.

The dispensing nozzle 11 has a longitudinally extending orifice 15 defined by an outlet tube 16 extending towards the cavity 10. An annular abutment 17 is formed within the orifice 15 part way along the outlet tube 16. The annular abutment 17 defines a small aperture 18 through which fluid can flow in use.

Two guides walls 20a, 20b extend into the cavity 10 from the second end wall 14 of the housing 9 to locate one end of the fluid discharging device 8 in the cavity 10 as will be described in more detail hereinafter.

Near to the first end wall 13 two apertures 21, 22 are formed in the side wall 12 on opposite sides of the housing 9 and towards a mid point of the housing 9 two longitudinally extending slots 23, 24 are formed in the side wall 12 in opposite sides of the housing 9.

The longitudinally extending slots 23, 24 are formed in the top and bottom sides of the housing 9 and the apertures 21, 22 are formed in the left and right sides of the housing 9 which, as shown, is substantially oval in cross-section.

It will be appreciated that the shape of the housing need not be oval it could be cylindrical or any other convenient shape.

The fluid discharging device 8 is in most respects conventional (e.g. taking the form of a conventional nasal pump) and will only be described briefly herein.

The fluid discharging device 8 has a hollow casing 30 defining a reservoir containing several doses of the fluid to be dispensed and a plunger slidingly engaged within the hollow casing 30.

The plunger is slideable in a chamber located within the hollow casing, the chamber being sized to accommodate a single dose of fluid. The plunger has a tubular portion 31 which is arranged to extend from a first end 32 of the hollow casing 30 for co-operation with the outlet tube 16 of the dispensing nozzle 11 and a piston (not shown) slidably supported in a chamber (not shown) located within and is attached to the hollow casing 30.

The release of the spring 40 from its compressed state causes relative movement between the hollow casing 30 and the plunger so as to eject a unit dose of fluid from the fluid reservoir into the dispensing nozzle 11.

The fluid is discharged through a discharge channel defined by the tubular portion 31 of the plunger into the dispensing nozzle 11.

The size of chamber is such that it accommodates a single dose of fluid, the diameter of the chamber and piston combined with the stroke of the plunger being such that a full stroke of the plunger in the chamber will produce a change in volume equal to a single dose of fluid.

The chamber is connected to the reservoir such that when the piston is moved by a return spring (not shown) into a start position a new dose of fluid is drawn into the cylinder ready for discharge. The re-setting of the spring 40 into its compressed state causes a new dose of fluid to be drawn into the chamber by allowing the piston to move to its start position.

The hollow casing 30 is slidingly supported within the cavity 10 defined by the housing 9 and is located at its first end 32 by the two guide walls 20a, 20b. The hollow casing 30 is of varying dimension along its length. In all there are three portions, a small end portion 34 at its first end 32, a large end portion 35 at its second end 33 and a middle portion 36 connecting the two end portions 34, 35.

At the juncture of the small end portion 34 with the middle portion 36 there is defined a first step 37 and at the juncture of the middle portion 36 with the large end portion 35 there is defined a second step 38.

The second step 38 is arranged to selectively co-operate in use with a complementary step 39 formed in the side wall 12 of the housing 9 to limit movement of the hollow casing 30 towards the dispensing nozzle 11.

A spring 40 is interposed between the second end 33 of the hollow casing 30 and the first end wall 13 of the housing 9 to bias the hollow casing 30 towards the dispensing nozzle 11. The spring 40 is interposed between the end wall 13 of the cavity 10 and a support platform 41 for the hollow casing 30.

As shown the spring 40 is in the form of a helical compression spring but it will be appreciated that other types of spring could be used such as rubber springs or gas springs.

The support platform 41 for the hollow casing 30 is interposed between the spring 40 and the second end 33 of the hollow casing 30.

The support platform 41 provides two functions it distributes the load from the spring into the second end 33 of the hollow casing and supports other components used as a locking means to selectively hold the spring in a compressed, cocked or set state. This enables a standard fluid discharging device to be used without modification.

Two detents 44a, 44b forming part of the locking means are also provided, each detent is connected to the support platform 41 by a flexible limb 43a, 43b.

The support platform 41 has a base portion 42 from which extend the two flexible limbs 43a, 43b supporting the two detents 44a, 44b forming part of the locking means. A location pip 46 is formed on the base portion 42 to centralise the spring 40 and a corresponding location pip 47 is formed on the first end wall 13 of the housing 9.

The locking means comprises of one or more detents, each of which is engageable with a respective aperture in a side wall of the body when the spring is in its compressed state. In the exemplary embodiment the locking means comprises of the two detents 44a, 44b and the two apertures 21, 22 in the housing 9.

Each of the detents 44a, 44b is engageable with one of the apertures 21, 22 to form a selectively releasable latch capable of holding the spring 40 in a compressed state. The two limbs 43a, 43b are elastically deformed by their containment within the cavity 10 and the force produced by this containment is used to bias the detents 44a, 44b into the apertures 21, 22.

Ideally, there are several detents positioned for engagement with respective apertures in opposite side walls of the body.

The two detents 44a, 44b are sized such that an outer portion 45 of each detent 44a, 44b projects outwardly from the side wall 12 of the housing 9 through which the detent 44a, 44b extends. Each detent 44a, 44b includes a portion 45 which extends outwardly from the side wall 12 with which the detent 44a, 44b is engaged to define a trigger that is operable by a user to release the spring 40 from its compressed state.

The outer portions 45 are therefore used by a user as a trigger to release the detents 44a, 44b from the apertures 21, 22 and hence release the locking means.

The end cap 7 is a tubular component which is closed at one end and has a thin flexible side wall 57. An inner surface 48 of the side wall 57 defines a cavity into which the body 6 is engaged to protect the dispensing nozzle 11. It is envisaged that the end cap may be attached to the body by a flexible strap or tether which could be moulded as part of the end cap and body.

The fitment of the protective end cap 7 to the body 6 causes the resetting of the spring 40 into its compressed state as will be described in more detail hereinafter. The hollow casing 30 has at least one outwardly extending detent for engagement with a complementary recess formed in the inner surface 48 of the end cap 7 so as to releasable hold the end cap 7 in position on the body 6. Each detent extends through a respective longitudinally extending slot in the body for engagement with the respective recess formed in the end cap.

The inner surface 48 of the exemplary embodiment has a recess 49 formed therein for co-operation with two detents 51 formed on the middle portion 36 of the hollow casing 30. The detents 51 and the groove 49 co-operate to provide a snap connection between the end cap 7 and the body 6. The snap connection is used to hold the end cap 7 on the body 6 when the fluid dispensing device 5 is in a stored or non-use condition.

The hollow casing 30 has at least one outwardly extending lug 52 for abutment with a complementary projection 50 formed on the inner surface 48 of the end cap 7 to provide a driving connection therebetween.

There are several lugs 52 formed on the hollow casing 30 for engagement with complementary projections formed on the inner surface 48 of the end cap 7, each of the lugs 52 being arranged to extend through a longitudinally extending slot formed in the side wall of the body.

The inner surface 48 of the end cap 7 of the exemplary embodiment has two projections 50 formed thereon for co-operation with two lugs 52 formed in the middle portion 36 of the hollow casing 30.

The two lugs 52 are positioned close to but are spaced away from the two detents 51. The two lugs 52 are further from the first end 32 of the hollow casing 30 than the two detents 51.

The two detents 51 have inclined surfaces 53 facing towards the first end 32 of the hollow casing 30 so that the projections 50 can easily ride up over them whereas the two lugs 52 have leading surfaces 54 facing towards the first end 32 of the hollow casing 30 that are substantially normal to the side wall 12 of the hollow casing 30.

The leading surfaces 54 of the lugs 52 form in combination with corresponding leading faces 56 on the projections 50 a driving connection between the end cap 7 and the hollow casing 30 which is used to re-set the spring mechanism.

The trailing faces 55 of the projections 50 are inclined so that the projections 50 can ride up over the detents 51 when the end cap 7 is pulled off of the body 6 to ready the fluid dispensing device 5 for use.

The detents 51 and the lugs 52 extend through the longitudinally extending slots 21 formed in the side wall 12 of the housing 9 for co-operation with the complementary recesses 49 and projections 50 in the end cap 7. The side wall 57 of the end cap 7 is sufficiently flexible to allow the end cap 7 to expand as it passes over the housing 9 and the corresponding tension placed into the side wall 57 of the end cap 7 is used to bias the detents 51 into the recesses 49.

Therefore it can seen that the exemplary embodiment discloses a fluid dispensing device comprising a body defining a cavity and a dispensing nozzle, a fluid discharging device housed in the cavity, the fluid discharging device having a hollow casing defining a reservoir containing a volume of fluid and a plunger slidingly engaged within the hollow casing, the plunger having a tubular portion which is arranged to extend from a first end of the hollow casing for co-operation with the dispensing nozzle, a spring interposed between a second end of the hollow casing and an end wall of the cavity to bias the hollow casing towards the dispensing nozzle and a locking means to hold the spring in a compressed state wherein upon release of the locking means the force stored in the spring is applied to the hollow casing thereby causing fluid to be ejected from the reservoir into the dispensing nozzle. Operation of the exemplary fluid dispensing device is as follows.

Figures 3, 4, 5:
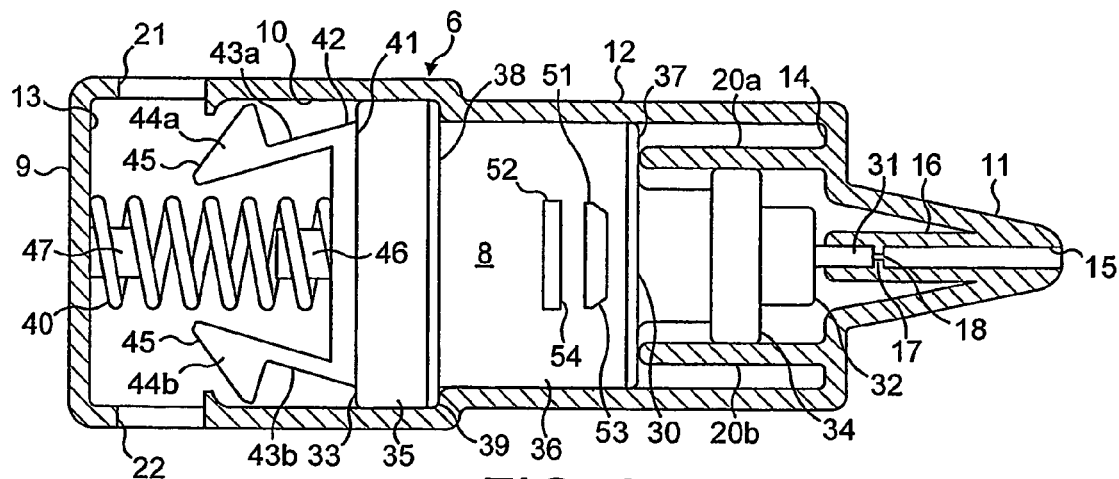
FIG. 3 is a plan view of a body forming part of the device shown in FIG. 1 in a discharged state.
FIG. 4 shows the body of FIG. 3 in a ready to discharge state.
FIG. 5 shows the body of FIG. 3 in a discharging state.
Figure 6:
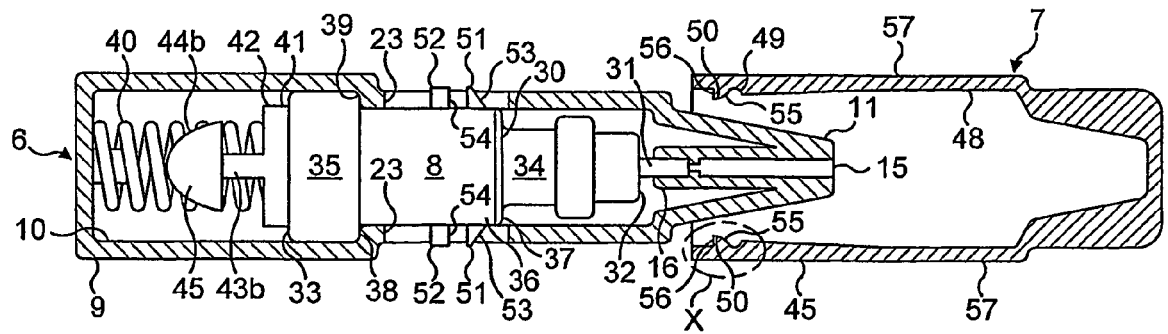
FIG. 6 is a side view of the device shown in FIG. 1 showing the device in a discharged state with a resetting procedure commencing.
Figure 7:
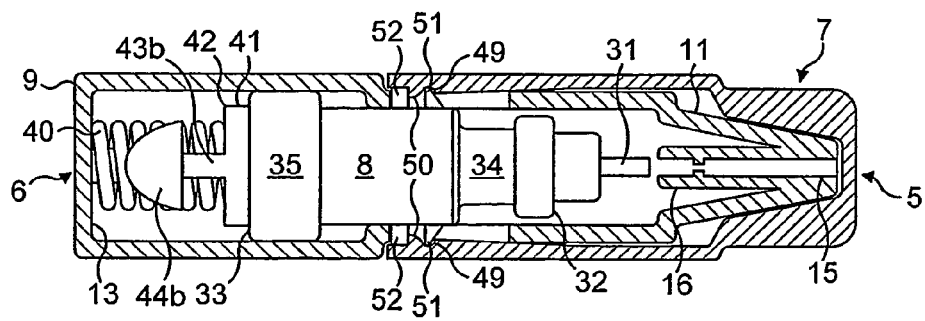
FIG. 7 is a view similar to that of FIG. 6 but showing the device after resetting and with a protective end cap in place.
Figure 8:
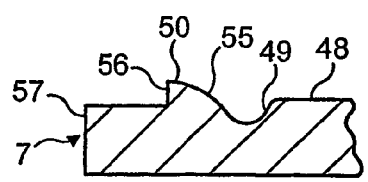
FIG. 8 is an enlarged scrap view of the area 'X' on FIG. 6.

FIG. 3 shows the fluid dispensing device 5 in a used or exhausted state. In this state the spring 40 is in a relaxed condition and little or no load is applied to the hollow casing 30 via the support platform 41.

In order to re-cock or reset the mechanism the hollow casing 30 must be moved towards the first end wall 13 so as to compress the spring 40. This re-setting or re-cocking is done by a replacing the end cap 7 onto the body 6.

As the end cap 7 is engaged with the body 6 the projections 50 on the inner surface 48 of the end cap 7 engage with the lugs 52 on the hollow casing 30. Further movement off the end cap 7 into engagement with the body 6 after this initial contact will result in the hollow casing 30 being moved towards the first end wall 13 of the housing 9 thereby compressing the spring 40.

This movement is continued by the user until the detents 44a, 44b engage with the apertures 21, 22 in the housing 9. In this position the mechanism is said to be in a set or cocked state and is ready for use.

During the action of resetting the mechanism the plunger is able to return to a starting position and this action causes a new dose of fluid to be drawn into the cylinder.

FIG. 4 shows the fluid dispensing device 5 in the re-set or cocked state.

To use the device the user has to firstly remove the end cap 7 from the body and place the free end of the dispensing nozzle into the orifice into which fluid is to be sprayed or dispensed.

To dispense the fluid the user then has to press the two triggers 45 inwardly to release the detents 44a, 44b from the apertures 21, 22. The disengagement of the detents 44a, 44b from the apertures 21, 22 allows the force stored in the spring 40 to be applied to the hollow casing 30. The application of this spring force causes the hollow casing 30 to move rapidly towards the second end wall 14 of the housing 9.

Initially, no fluid will be dispensed because the end of the tubular portion 31 of the plunger is not in contact with any other structure. This is because the movement of the hollow casing 30 between the exhausted and re-set positions is greater than the stroke of the piston in the cylinder.

However when the end of the hollow portion 31 of the plunger contacts the annular abutment 17 in the outlet tube 16 any further movement of the hollow casing 30 towards the second end wall 14 will result in a corresponding relative movement between the hollow casing 30 and the plunger.

This relative movement between the hollow casing 30 and the plunger will result in a corresponding movement of the piston in the cylinder and consequently any fluid contained within the cylinder will be ejected out of the cylinder into the hollow portion 31 of the plunger and from there via the aperture 19 in the annular abutment 18 into the orifice 15 in the dispensing nozzle 11.

Because of the free travel in the mechanism due to the difference in the stroke of the piston and the travel the hollow casing 30, a short travel but fast acting motion is applied to the piston. This action results in a rapid ejection of the fluid from the chamber with the result that a good atomisation of the fluid is produced as it exits the dispensing nozzle 11.

In addition, because the dispensing of the fluid is solely dependent upon the action of the spring upon the hollow casing it is far more repeatable and reliable than a system reliant upon the force and speed of application of a force by a user.

By using the end cap to re-set or re-cock the spring the user knows that as soon as the end cap is removed the device is ready to discharge fluid and no other action is required.

In addition, because it is usual for a user to replace the end cap onto the body after each use, the user does not have to remember to re-set the device, the action of replacing the end cap automatically completes this procedure.

Although the invention has been described in relation to a device having a fluid discharging device sealed within the housing it will be appreciated that the housing could have a removable end or be openable in some other manner to allow the fluid discharging device to be replaced.

It will be further appreciated that the use of a support platform is not essential and that if required the hollow casing could be designed such that the biasing means could act directly thereupon. In addition, the hollow casing could be made such that the detents used to hold the biasing means in a compressed state are connected directly to the hollow casing via flexible limbs formed as part of the hollow casing.

A fluid dispensing apparatus for housing a fluid discharging device forming a second aspect of the invention is also disclosed. The fluid dispensing apparatus is in all respects the same as the fluid dispensing device previously described with the exception that it does not contain a fluid discharging device.

The fluid discharging apparatus therefore comprises of a body defining a cavity, a dispensing nozzle, biasing means housed in the cavity and a locking means to selectively hold the biasing means in a compressed state, wherein, in use, a fluid discharging device is positioned between the biasing means and the dispensing nozzle.

In use the release of the locking means will cause the force stored in the biasing means to be applied to a fluid discharging device so as to bias the fluid discharging device towards the dispensing nozzle.

The fluid dispensing apparatus further comprises an end cap for engagement with the body, the end cap being adapted such that, in use, engagement of the end cap onto the body will cause compression of the biasing means.

It is envisaged that the fluid discharging apparatus could be sold as an item into which a fluid discharging device is fitted by a user or pharmacist.

Administration of medicament may be indicated for the treatment of mild, moderate or severe acute or chronic symptoms or for prophylactic treatment. It will be appreciated that the precise dose administered will depend on the age and condition of the patient, the particular medicament used and the frequency of administration and will ultimately be at the discretion of the attendant physician. When combinations of medicaments are employed the dose of each component of the combination will in general be that employed for each component when used alone.

Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (eg as the sodium salt), ketotifen or nedocromil (eg as the sodium salt); anti-infectives e.g., cephalosporins, penicillins, streptomycin, sulphonamides, tetracyclines and pentamidine; antihistamines, e.g., methapyrilene; anti-inflammatories, e.g., beclomethasone (eg as the dipropionate ester), fluticasone (eg as the propionate ester), flunisolide, budesonide, rofleponide, mometasone (eg as the furoate ester), ciclesonide, triamcinolone (eg as the acetonide), $6\alpha,9\alpha$-difluoro-$11\beta$-hydroxy-$16\alpha$-methyl-3-oxo-$17\alpha$-propionyloxy-androsta-1,4-diene-$17\beta$-carbothioic acid S-(2-oxo-tetrahydro-furan-3-yl)ester or $6\alpha,9\alpha$-Difluoro-$17\alpha$-[(2-furanylcarbonyl)oxy]-$11\beta$-hydroxy-$16\alpha$-methyl-3-oxo-and rosta-1,4-diene-$17\beta$-carbothioic acid S-fluoromethyl ester; antitussives, e.g., noscapine; bronchodilators, e.g., albuterol (eg as free base or sulphate), salmeterol (eg as xinafoate), ephedrine, adrenaline, fenoterol (eg as hydrobromide), formoterol (eg as fumarate), isoprenaline, metaproterenol, phenylephrine, phenylpropanolamine, pirbuterol (eg as acetate), reproterol (eg as hydrochloride), rimiterol, terbutaline (eg as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; PDE4 inhibitors eg cilomilast or roflumilast; leukotriene antagonists eg montelukast, praniukast and zafirlukast; [adenosine 2a agonists, eg 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate)]*; [α4 integrin inhibitors eg (2S)-3-[4-({[4-(aminocarbonyl)-1-piperidinyl]carbonyl}oxy)phenyl]-2-[((2S)-4-methyl-2-{[2-(2-methylphenoxy)acetyl]amino}pentanoyl)amino]propanoic acid (e.g as free acid or potassium salt)]*, diuretics, e.g., amiloride; anticholinergics, e.g., ipratropium (eg as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagons. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament and/or to minimise the solubility of the medicament in the propellant.

Preferably, the medicament is an anti-inflammatory compound for the treatment of inflammatory disorders or diseases such as asthma and rhinitis.

In one aspect, the medicament is a glucocorticoid compound, which has anti-inflammatory properties. One suitable glucocorticoid compound has the chemical name: $6\alpha,9\alpha$-Difluoro-$17\alpha$-(1-oxopropoxy)-$11\beta$-hydroxy-$16\alpha$-methyl-3-oxo-androsta-1,4-diene-$17\beta$-carbothioic acid S-fluoromethyl ester (fluticasone propionate). Another suitable glucocorticoid compound has the chemical name: $6\alpha,9\alpha$- difluoro-17α-[(2-furanylcarbonyl)oxy]-11β,-hydroxy-16α-methyl-3-oxo-androsta-1,4-diene-17β-carbothioic acid S-fluoromethyl ester. A further suitable glucocorticoid compound has the chemical name: 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester.

Other suitable anti-inflammatory compounds include NSAIDs e.g. PDE4 inhibitors, leukotriene antagonists, iNOS inhibitors, tryptase and elastase inhibitors, beta-2 integrin antagonists and adenosine 2a agonists.

The medicament is formulated as any suitable fluid formulation, particularly a solution (e.g. aqueous) formulation or a suspension formulation, optionally containing other pharmaceutically acceptable additive components.

Suitable formulations (e.g. solution or suspension) may be stabilised (e.g. using hydrochloric acid or sodium hydroxide) by appropriate selection of pH. Typically, the pH will be adjusted to between 4.5 and 7.5, preferably between 5.0 and 7.0, especially around 6 to 6.5.

Suitable formulations (e.g. solution or suspension) may comprise one or more excipients. By the term "excipient", herein, is meant substantially inert materials that are non-toxic and do not interact with other components of a composition in a deleterious manner including, but not limited to, pharmaceutical grades of carbohydrates, organic and inorganic salts, polymers, amino acids, phospholipids, wetting agents, emulsifiers, surfactants, poloxamers, pluronics, and ion exchange resins, and combinations thereof.

Suitable carbohydrates include monosaccharides include fructose; disaccharides, such as, but not limited to lactose, and combinations and derivatives thereof; polysaccharides, such as, but not limited to, cellulose and combinations and derivatives thereof; oligosaccharides, such as, but not limited to, dextrins, and combinations and derivatives thereof; polyols, such as but not limited to sorbitol, and combinations and derivatives thereof.

Suitable organic and inorganic salts include sodium or calcium phosphates, magnesium stearate, and combinations and derivatives thereof.

Suitable polymers include natural biodegradable protein polymers, including, but not limited to, gelatin and combinations and derivatives thereof; natural biodegradable polysaccharide polymers, including, but not limited to, chitin and starch, crosslinked starch and combinations and derivatives thereof; semisynthetic biodegradable polymers, including, but not limited to, derivatives of chitosan; and synthetic biodegradable polymers, including, but not limited to, polyethylene glycols (PEG), polylactic acid (PLA), synthetic polymers including but not limited to polyvinyl alcohol and combinations and derivatives thereof;

Suitable amino acids include non-polar amino acids, such as leucine and combinations and derivatives thereof. Suitable phospholipids include lecithins and combinations and derivatives thereof.

Suitable wetting agents, surfactants and/or emulsifiers include gum acacia, cholesterol, fatty acids including combinations and derivatives thereof. Suitable poloxamers and/or Pluronics include poloxamer 188, Pluronic® F-108, and combinations and derivations thereof. Suitable ion exchange resins include amberlite IR120 and combinations and derivatives thereof;

Suitable solution formulations may comprise a solubilising agent such as a surfactant. Suitable surfactants include α-[4-(1,1,3,3-tetramethylbutyl)phenyl]-ω-hydroxypoly(oxy-1,2-ethanediyl)polymers including those of the Triton series e.g. Triton X-100, Triton X-114 and Triton X-305 in which the X number is broadly indicative of the average number of ethoxy repeating units in the polymer (typically around 7-70, particularly around 7-30 especially around 7-10) and 4-(1,1,3,3-tetramethylbutyl)phenol polymers with formaldehyde and oxirane such as those having a relative molecular weight of 3500-5000 especially 4000-4700, particularly Tyloxapol. The surfactant is typically employed in a concentration of around 0.5-10%, preferably around 2-5% w/w based on weight of formulation.

Suitable solution formulations may also comprise hydroxyl containing organic co-solvating agents include glycols such as polyethylene glycols (eg PEG 200) and propylene glycol; sugars such as dextrose; and ethanol. Dextrose and polyethylene glycol (eg PEG 200) are preferred, particularly dextrose. Propylene glycol is preferably used in an amount of no more than 20%, especially no more than 10% and is most preferably avoided altogether. Ethanol is preferably avoided. The hydroxyl containing organic co-solvating agents are typically employed at a concentration of 0.1-20% e.g. 0.5-10%, e.g. around 1-5% w/w based on weight of formulation.

Suitable solution formulations may also comprise solubilising agents such as polysorbate, glycerine, benzyl alcohol, polyoxyethylene castor oils derivatives, polyethylene glycol and polyoxyethylene alkyl ethers (e.g. Cremophors, Brij).

Suitable solution formulations may also comprise one or more of the following components: viscosity enhancing agents; preservatives; and isotonicity adjusting agents.

Suitable viscosity enhancing agents include carboxymethylcellulose, veegum, tragacanth, bentonite, hydroxypropylmethylcellulose, hydroxypropylcellulose, hydroxyethylcellulose, poloxamers (e.g. poloxamer 407), polyethylene glycols, alginates xanthym gums, carageenans and carbopols.

Suitable preservatives include quaternary ammonium compounds (e.g. benzalkonium chloride, benzethonium chloride, cetrimide and cetylpyridinium chloride), mercurial agents (e.g. phenylmercuric nitrate, phenylmercuric acetate and thimerosal), alcoholic agents (e.g. chlorobutanol, phenylethyl alcohol and benzyl alcohol), antibacterial esters (e.g. esters of para-hydroxybenzoic acid), chelating agents such as disodium edetate (EDTA) and other anti-microbial agents such as chlorhexidine, chlorocresol, sorbic acid and its salts and polymyxin.

Suitable isotonicity adjusting agents act such as to achieve isotonicity with body fluids (e.g. fluids of the nasal cavity), resulting in reduced levels of irritancy associated with many nasal formulations. Examples of suitable isotonicity adjusting agents are sodium chloride, dextrose and calcium chloride.

Suitable suspension formulations comprise an aqueous suspension of particulate medicament and optionally suspending agents, preservatives, wetting agents or isotonicity adjusting agents.

The particulate medicament suitably has a mass mean diameter (MMD) of less than 20 μm, preferably between 0.5-10 μm, especially between 1-5 μm. If particle size reduction is necessary, this may be achieved by techniques such as micronisation and/or microfluidisation.

Suitable suspending agents include carboxymethylcellulose, veegum, tragacanth, bentonite, methylcellulose and polyethylene glycols.

Suitable wetting agents function to wet the particles of medicament to facilitate dispersion thereof in the aqueous phase of the composition. Examples of wetting agents that can be used are fatty alcohols, esters and ethers. Preferably, the wetting agent is a hydrophilic, non-ionic surfactant, most preferably polyoxyethylene (20) sorbitan monooleate (supplied as the branded product Polysorbate 80).

Suitable preservatives and isotonicity adjusting agents are as described above in relation to solution formulations.

The dispensing device herein is suitable for dispensing fluid medicament formulations for the treatment of inflammatory and/or allergic conditions of the nasal passages such as rhinitis e.g. seasonal and perennial rhinitis as well as other local inflammatory conditions such as asthma, COPD and dermatitis.

A suitable dosing regime would be for the patient to inhale slowly through the nose subsequent to the nasal cavity being cleared. During inhalation the formulation would be applied to one nostril while the other is manually compressed. This procedure would then be repeated for the other nostril. Typically, one or two inhalations per nostril would be administered by the above procedure up to three times each day, ideally once daily. Each dose, for example, may deliver 5 µg, 50 µg, 100 µg, 200 µg or 250 µg of active medicament. The precise dosage is either known or readily ascertainable by those skilled in the art.

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following. claims:

The invention claimed is:

1. A fluid dispensing device comprising a body defining a cavity and a dispensing nozzle, a protective end cap having an inner surface for engagement with the body to protect the dispensing nozzle, a fluid discharging device housed in the cavity for reciprocal movement between a rest position and an actuated position, the fluid discharging device having a hollow casing defining a reservoir for containing a volume of fluid and a plunger slidingly engaged within the hollow casing for movement relative to the hollow casing, the plunger having a tubular portion through which fluid is able to be ejected from the fluid discharging device when the plunger moves relative to the hollow casing and which extends from a first end of the hollow casing for co-operation with the dispensing nozzle, biasing means interposed between a second end of the hollow casing and an end wall of the cavity to bias the hollow casing towards the dispensing nozzle to move the fluid discharging from the rest position to the actuated position and cause relative movement of the plunger to the hollow casing, and a locking means to hold said biasing means in a compressed state wherein upon release of the locking means the force stored in the biasing means is applied to the hollow casing to move the fluid discharging device from its rest position to its actuated position thereby causing fluid to be ejected from the reservoir through the tubular portion of the plunger into the dispensing nozzle, wherein the fluid dispensing device is adapted to enable the fluid discharging device to return to its rest position from its actuated position against the bias of the biasing means and wherein the hollow casing has at least one outwardly extending detent for engagement with a complementary recess formed in the inner surface of the end cap so as to releasably hold the end cap in position on the body.

2. A device as claimed in claim 1 in which the release of the biasing means from its compressed state causes relative movement between the hollow casing and the plunger so as to eject a unit dose of fluid from the fluid reservoir into the dispensing nozzle.

3. A device as claimed in claim 1 in which the plunger is slideable in a chamber located within the hollow casing, the chamber being sized to accommodate a single dose of fluid.

4. A device as claimed in claim 3 in which the re-setting of the biasing means into its compressed state causes a new dose of fluid to be drawn into the chamber.

5. A device as claimed in claim 1 in which the reservoir contains several doses of fluid.

6. A device as claimed in claim 1 in which the locking means comprises of one or more detents, each of which is engageable with a respective aperture in a side wall of the body when the biasing means is in its compressed state.

7. A device as claimed in claim 6 in which there are several detents positioned for engagement with respective apertures in opposite side walls of the body.

8. A device as claimed in claim 1 in which the biasing means is interposed between the end wall of the cavity and a support platform for the hollow casing.

9. A device as claimed in claim 8, in which the locking means comprises of one or more detents, each of which is engageable with a respective aperture in a side wall of the body when the biasing means is in its compressed state, and in which each detent is connected to the support platform by a flexible limb.

10. A device as claimed in claim 6 in which each detent is connected to the hollow casing by a flexible limb.

11. A device as claimed in claim 6 in which each detent includes a portion which extends outwardly from the side wall with which the detent is engaged to define a trigger that is operable by a user to release the biasing means from its compressed state.

12. A device as claimed in claim 1, wherein the fitment of the protective end cap to the body causes the resetting of the biasing means into its compressed state.

13. A device as claimed in claim 1 in which the hollow casing has at least one outwardly extending lug for abutment with a complementary projection formed on the inner surface of the end cap to provide a driving connection therebetween.

14. A device as claimed in claim 13 in which the body has at least one longitudinally extending slot through which a respective lug extends.

15. A device as claimed in claim 14 in which there are several lugs formed on the hollow casing for engagement with complementary projections formed on the inner surface of the end cap, each of the lugs being arranged to extend through a longitudinally extending slot formed in the side wall of the body.

16. A device as claimed in claim 1 in which each detent extends through a respective longitudinally extending slot in the body for engagement with the respective recess formed in the end cap.

17. A fluid dispensing device as claimed in claim 1 wherein said reservoir contains a volume of fluid medicament formulation.

18. A device as claimed in claim 17, wherein said fluid medicament formulation is in the form of a solution formulation.

19. A device as claimed in claim 17, wherein said fluid medicament formulation is in the form of a suspension formulation.

20. A device as claimed in claim 17, wherein the fluid medicament formulation comprises an anti-inflammatory medicament compound.

21. A device as claimed in claim 20, wherein said medicament compound is a glucocorticoid compound.

22. A device as claimed in claim 21, wherein said glucocorticoid compound is selected from the group consisting of 6α,9α-Difluoro-17α-(1-oxopropoxy)-11β-hydroxy-16α-methyl-3-oxo-androsta-1,4-diene-17β-carbothioic acid S-fluoromethyl ester; 6α,9α-difluoro-17α-[(2-furanylcarbonyl)oxy]-11β-hydroxy-16α-methyl-3-oxo-androsta-1,4-diene-17β-carbothioic acid S-fluoromethyl ester; and 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester.

23. A device as claimed in claim 20, wherein said medicament compound is selected from the group consisting of PDE4 inhibitors, leukotriene antagonists, iNOS inhibitors, tryptase and elastase inhibitors, beta-2 integrin antagonists and adenosine 2a agonists.

\* \* \* \* \*